US012703673B2

(12) United States Patent
Andrusiak et al.

(10) Patent No.: US 12,703,673 B2
(45) Date of Patent: Aug. 11, 2026

(54) METHOD FOR SYNTHESIZING XANTHOHUMOL

(71) Applicant: PRO XN SP. Z O. O., Warsaw (PL)

(72) Inventors: Joanna Andrusiak, Badkowo (PL); Kinga Mylkie, Kikol (PL); Andrzej Jan Wolan, Torun (PL); Mariusz Jan Bosiak, Torun (PL)

(73) Assignee: PRO XN SP. Z O.O., Warsaw (PL)

( * ) Notice: Subject to any disclaimer, the term of this patent is extended or adjusted under 35 U.S.C. 154(b) by 451 days.

(21) Appl. No.: 18/289,578

(22) PCT Filed: May 7, 2021

(86) PCT No.: PCT/EP2021/062142

§ 371 (c)(1),
(2) Date: Nov. 6, 2023

(87) PCT Pub. No.: WO2022/233428

PCT Pub. Date: Nov. 10, 2022

(65) Prior Publication Data

US 2024/0239732 A1 Jul. 18, 2024

(51) Int. Cl.
*C07C 45/60* (2006.01)
*C07D 311/74* (2006.01)

(52) U.S. Cl.
CPC ............ *C07C 45/60* (2013.01); *C07D 311/74* (2013.01)

(58) Field of Classification Search
CPC .............................. C07C 45/50; C07D 311/74
See application file for complete search history.

(56) References Cited

U.S. PATENT DOCUMENTS

| | | | |
|---|---|---|---|
| 9,617,213 B2 * | 4/2017 | Rossello ............. | C07D 311/04 |
| 2016/0075652 A1 | 3/2016 | Rossello et al. | |

FOREIGN PATENT DOCUMENTS

| | | |
|---|---|---|
| CN | 110117327 A | 8/2019 |
| WO | 2009026206 A1 | 2/2009 |

OTHER PUBLICATIONS

Polish Search Report for Application No. NP P432129 Mailed on Aug. 24, 2020.

* cited by examiner

*Primary Examiner* — Sikarl A Witherspoon
(74) *Attorney, Agent, or Firm* — Rivka Friedman

(57) ABSTRACT

A method for synthesizing xanthohumol (XN) from naringenin comprising includes the steps of acylating hydroxyl groups of a naringenin flavone moiety to obtain an acylation product, a reaction of conversion of the flavone moiety into a chalcone moiety, and subjecting the chalcone compound to a reaction of hydrolysis of its ester groups, and next to a reaction of substitution of a prenyl moiety of the chalcone moiety to obtain xanthohumol. The xanthohumol produced by this method can be purified using crystallisation.

12 Claims, 1 Drawing Sheet

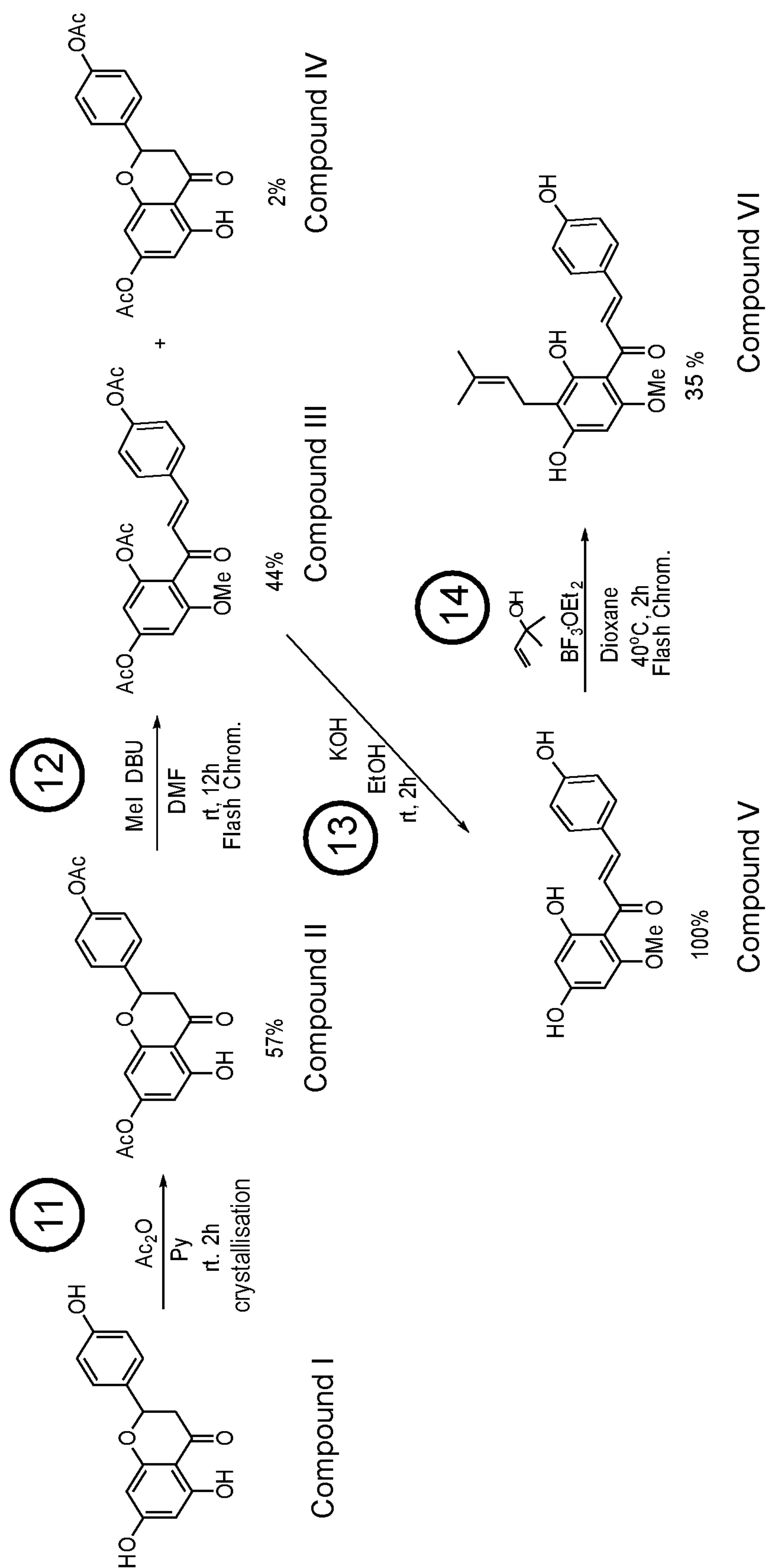
Compound I
Compound II
Compound III
Compound IV
Compound V
Compound VI

METHOD FOR SYNTHESIZING XANTHOHUMOL

TECHNICAL FIELD

The invention relates to a method for synthesizing xanthohumol (XN).

BACKGROUND

Xanthohumol (2',4,4'-trihydroxy-6'-methoxy-3'-prenylchalcone), referred to as XN, is a member of a group of prenylated flavonoids having a beneficial effect on animal organisms, including humans.

Xanthohumol neutralizes free radicals (it is an antioxidant) and prevents the development of arteriosclerosis and cancer. Antioxidant properties of XN are important given that its activity as the free-radical acceptor (free radical scavenger), for hydroxyl and peroxide free-radicals, is several fold greater than that of the standard one, i.e.: Trolox® (6-hydroxy-2,5,7,8-tetramethylchromate-2-carboxylic acid). Moreover, XN, unlike its isomer, isoxanthohumol (IXN), also exhibits antioxidant activity against superoxide anion radicals, generated by xanthine oxidase, without directly inhibiting the activity of the latter.

XN also has antimicrobial and antiviral activity, i.a. it inhibits the development of moulds and the growth of bacteria which leads to e.g. purulent skin infections and systemic infections of staphylocococcal etiology. XN also inhibits the development of cells causing tooth decay and has an antimalarial effect.

A particular property of XN is its anticancer effect, including antiproliferative properties: inhibition of DNA synthesis, disruption of cell cycle in cells with impaired apoptosis ability as well as antiangiogenic properties.

Accordingly, XN is used as an ingredient in various compositions, including pharmaceutical compositions, including drugs and dietary supplements. XN is also an ingredient in healthy food and beverages, as well as in various cosmetic compositions, including cosmetic compositions for external application—on the skin, as their active component.

Known methods for obtaining xanthohumol include its isolation from natural raw materials and chemical synthesis that makes it possible to obtain synthetic XN.

A well-known natural raw material from which xanthohumol is isolated is hop flowers, which contain on average from 0.1 to 1% XN, depending on the variety. The methods for isolating natural XN involve a multi-step and time-consuming extraction yielding an XN extract contaminated with various substances, the removal of which using inexpensive crystallisation methods is heavily limited. Hence, the extracts are then separated on a chromatographic column to isolate pure XN. However, the chromatographic purification method involves a low, unsatisfactory yield and high equipment costs, so that the methods above are not used on an industrial scale.

Chemical methods for obtaining synthetic XN are also known that are characterised by slightly higher yield. The route of chemical synthesis of XN is determined by the choice of the substrate for synthesis (starting compound), which should be inexpensive and easily accessible. However, XN chemical synthesis methods hitherto known also require chromatographic separation of the post-reaction mixture in order to isolate pure xanthohumol due to the by-products produced, such as for example various XN isomers that cannot be separated using crystallisation methods.

For example, a six-step method is known for synthetically obtaining XN from 2,'4',6'-tri-hydroxyacetophenone (1-acetylphloroglucinol), wherein in the first step said compound is methoxymethylated to protect hydroxyl groups in positions 4' and 6'. The 2'-hydroxy-4',6'-dimethoxymethylacetophenone obtained in this step is then subjected to the Mitsunobu reaction, wherein the prenyl group donor is 3-methyl-2-buten-1-ol, and the product is prenylated ether, from which xanthohumol is produced.

Another known method of XN synthesis includes the alkylation reaction using 3,3-dimethylallyl bromide. In this method, the prenylated ether in the third step is subjected to sigmatropic Claisen rearrangement in order to attach the prenyl group to the aryl ring, followed by methylation of the free hydroxyl group. In the next step, the resulting prenylated ketone is subjected to a Claisen-Schmidt reaction, involving aldol condensation with 4-hydroxy-benzoic aldehyde, comprising a blocked hydroxyl group that enables a chalcone backbone to be formed. In the last step, protective methoxymethyl groups are removed from the prenylated chalcone to obtain xanthohumol. Total yield of this xanthohumol synthesis is approximately 10%.

Due to the significantly improved yield of the process of preparing XN by way of chemical synthesis, compared to methods of its extraction from plant material, various aspects of synthetic XN have been tested in order to determine whether it has the same effect as the natural, isolated XN. These tests demonstrated that synthetic XN is in no respects different than the natural XN. In particular, synthetic XN inhibits cancer cell proliferation and has antioxidant activity.

Methods of chemical synthesis of XN, using various substrates, are also known from patent literature. For example, the publication of the international application WO2009026206 discloses the route of XN synthesis from 1-acetylphloroglucinol as the starting substrate, but said reaction is multi-step and yields, apart from XN, a by-product that has much lower biological activity than XN. In order to obtain pure XN, the products of said reaction are subjected to chromatographic separation, which increases the cost of the procedure.

SUMMARY

There is still a need to modify the known XN chemical synthesis routes in order to improve the yield thereof and to reduce, on the route of XN synthesis, side reactions leading to the formation of undesirable products that are incapable of crystallisation separation, and which may only be separated from XN by way of chromatographic separation.

It would therefore be expedient to develop an XN chemical synthesis with improved XN yield and increased purity of the final product so as to reduce and, more preferably, to completely eliminate the need for chromatographic separation of the synthesis product in order to obtain pure XN.

There is disclosed a method for synthesizing xanthohumol (XN) involving synthesizing xanthohumol from naringenin in a process comprising steps of providing naringenin, acylating hydroxyl groups at carbons 7 and 4' of a naringenin flavone moiety to obtain an acylation product, subjecting the acylation product to a reaction of alkylation of a free hydroxyl to an alkoxyl moiety and to a reaction of conversion of the flavone moiety into a chalcone moiety, in the presence of a non-nucleophilic base, in a polar aprotic solvent, to obtain a chalcone compound; next subjecting the chalcone compound to: a reaction of hydrolysis of its ester groups at carbons 4, 4' and 6 of the chalcone moiety to obtain hydroxyl groups, and next a reaction of substitution of a prenyl moiety at carbon 5' of the chalcone moiety to obtain xanthohumol.

Preferably, the step of acylating is carried out using acetic anhydride.

Preferably, the acylation product is purified by way of crystallisation.

Preferably, the reaction of alkylation is carried out using an alkylating agent selected from the group consisting of C1-C8 alkyl iodides and bromides.

Preferably, the reaction of alkylation is carried out using the alkylating agent selected from the group consisting of methyl iodide and methyl bromide.

Preferably, the reaction of conversion of the flavone moiety into the chalcone moiety is carried out in the presence of a non-nucleophilic base selected from the group consisting of: 1,8-diazabicyclo[5.4.0]undec-7-ene (DBU), 1,4-diazabicyclo[2.2.2]octane (DABCO) and 4-(N,N-dimethylamino)pyridine (DMAP).

Preferably, the reaction of conversion of the flavone moiety into the chalcone moiety is carried out in a polar aprotic solvent selected from the group consisting of: dimethylformamide (DMF), N-methylpyrrolidone (NMP) and dimethylacetamide (DMAc).

Preferably, the obtained chalcone compound is subjected to the hydrolysis reaction carried out using ethyl alcohol in an alkaline medium.

Preferably, the substitution reaction of the prenyl moiety is carried out using a prenylating agent comprising 1,1-dimethylallyl moiety.

Preferably, the prenylating agent used is 1,1-dimethylallyl alcohol or acetic acid ester of 1,1-dimethylallylalcohol.

Preferably, the substitution reaction of the prenyl moiety is carried out in the presence of boron trifluoride etherate ($BF_3 \cdot O(CH_2CH_3)_2$) in dioxane, at elevated temperature.

Preferably, the substitution reaction is carried out at a temperature of 40° C.

The developed method of XN synthesis features not only improved product yield, but also high purity of the obtained XN. The xanthohumol produced by this method can be purified using less expensive crystallisation methods, without the need to use chromatographic separation.

Such an effect was achieved by selecting a substrate suitable for the XN synthesis, which according to the inventive method is naringenin. Naringenin is a readily available and relatively inexpensive raw material. Moreover, the developed conditions for reactions involving naringenin provide significant reduction of the reactions producing by-products, including those requiring chromatographic separation to be removed.

The advantages indicated above, i.e. improved synthesis yield and high purity of the product enable one to use the developed method of XN synthesis not only on a laboratory scale, but also on a semi-technical or industrial scale, ensuring a reduction in production costs, compared to known methods.

Due to its cost-effectiveness, the method according to the invention is in particular suitable for industrial-scale implementation.

BRIEF DESCRIPTION OF DRAWINGS

These and other objects of the invention presented herein are accomplished by providing a method for synthesizing xanthohumol (XN). Further details and features of the present invention, its nature and various advantages will become more apparent from the following detailed description of the preferred embodiments shown in a drawing, in which:

FIG. 1 shows an example of the synthesis route of XN according to the invention.

Reference numbers used in the drawing:

- 11—acylation reaction,
- 12—alkylation reaction and reaction of conversion of flavone moiety into chalcone moiety (involving opening of the ring),
- 13—hydrolysis reaction,
- 14—reaction of the prenyl group substitution.

DETAILED DESCRIPTION

The following detailed description is of the best currently contemplated modes of carrying out the invention. The description is not to be taken in a limiting sense, but is made merely for the purpose of illustrating the general principles of the invention.

According to the invention, xanthohumol is produced from naringenin—as a substrate—compound I. Naringenin (CAS no. of the compound: 480-41-1) is a flavonoid present in various fruits, e.g. in grapefruit juice and seeds of ripe peach fruit. The process of isolating naringenin from plant material is simple and efficient, making naringenin readily available and relatively inexpensive.

In the method according to the invention, natural and/or synthetic naringenin may be used as a substrate in XN synthesis. The origin of the substrate does not affect the yield of the final product: XN. In its structure, naringenin comprises a flavone moiety for which the carbon numbering is shown below, for greater clarity of the indications used hereinbelow.

Flavone Moiety Carbon Numbering:

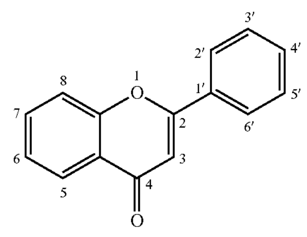 [SMILES: O=c1cc(-c2ccccc2)oc2ccccc12]

As illustrated in FIG. 1, the first step of the developed method involves the acylation reaction of naringenin: reaction 11. Reaction 11 is carried out under conditions that allow the substitution of the acyl moiety into hydroxyl moieties in positions 7 and 4' of the naringenin flavone moiety.

For example, acylation may be carried out using acetic anhydride ($Ac_2O$) in a pyridine (Py) medium at room temperature. The acylation product, marked in FIG. 2 as compound II, is preferably purified, for example by way of crystallisation. Under such conditions, the acylation reaction yields compound II at 57%.

The reaction is selective, since the hydroxyl group in position 5 in the naringenin molecule is bound by an intramolecular hydrogen bond with oxygen of the carbonyl group at carbon 4 of the naringenin flavone moiety. Due to this phenomenon, if an appropriate ratio of reagents is used, the hydroxyl groups at carbons 7 and 4' of the naringenin flavone moiety are first subjected to acylation reaction.

The acylation product (compound II) is then subjected to reaction 12. This reaction includes selective alkylation of the hydroxyl (—OH) moiety of compound II, at carbon 5 of the flavone moiety, and opening the ring of the flavone moiety to form a chalcone structure, obtaining a chalcone compound as the main product of the reaction, marked in FIG. 1 as compound III. For greater clarity of the indications used in the description, the carbon numbering of the chalcone moiety is shown below.

Carbon Numbering of the Chalcone Moiety Obtained in Reaction 12:

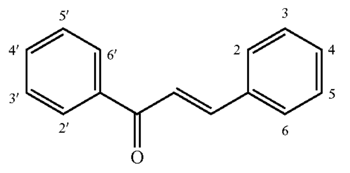 [SMILES: O=C(/C=C/c1ccccc1)c1ccccc1]

In reaction 12 one may use various alkylating agents, i.e. alkyl moiety (R) donors allowing the alkylation of the hydroxyl moiety of compound II, involving the formation of an alkoxy (—OR) moiety, under the conditions of the reaction carried out. For example, an alkyl halide, preferably such as alkyl iodide or alkyl bromide may be used as the alkylating agent. More preferably, methyl halides such as methyl bromide, and more preferably methyl iodide (Mel) are used as the alkylating agent.

The use of alkyl iodide, and more preferably methyl iodide (Mel) in the alkylation reaction, provides an additional improvement of reaction 12 yield, wherein reaction 12 with methyl iodide features optimal yield.

Reaction 12 is carried out in a polar aprotic solvent medium. The aprotic polar solvent used may constitute a solvent or mixture of two or more different solvents, and preferably at least one polar aprotic solvent selected from a group consisting of: dimethylformamide (DMF), N-methylpyrrolidone (NMP) and N,N-dimethylacetamide (DMAc).

Reaction 12 is carried out at a pH range between 7 and 12, using a non-nucleophilic base, preferably one or more non-nucleophilic bases selected from a group consisting of: 1,8-diazabicyclo[5.4.0]undec-7-ene (DBU), 1,4-diazabicyclo[2.2.2]octane (DABCO) and 4-(N,N-dimethylamino) pyridine (DMAP).

Reaction 12 may be carried out at room temperature, for the time necessary for compound II to react to compound III, which preferably is approximately 12 hours. However, more preferably, the reaction is carried out at an elevated temperature, which shortens the reaction time, for example, at 50° C. the reaction is carried out for 2 hours until the product is obtained. The obtained product may be purified, preferably using column chromatography. Under such conditions the yield of product compound III is obtained at 44%. As a by-product, at a low yield of approximately 2%, compound IV is also obtained, a product of alkylation, e.g. of methylation, without opening the flavone ring.

The acetyl group (—OAc) formed at carbon 6' in reaction 12 derives from other substrate molecules. An $E2C_B$ elimination reaction is followed by the opening of the flavone ring, and the formed phenolate anion reacts with alkyl iodide. The hydroxyl group is then transacetylated at position 5 involving a substrate molecule.

Also preferably, the reaction 12, i.e. the reaction involving a non-nucleophilic base, as indicated above, as well as methyl iodide (Mel) and acetic anhydride as the acylating agent, is carried out in solvents selected from the group of dichloromethane, chloroform, tetrahydrofuran, N,N-dimethylformamide, and/or N-methylpyrrolidone. In this case, the acylating agent derives from an external source, so that the results obtained in reaction 12 are more reproducible.

The alkylation reaction and the flavone ring opening reaction may also be carried out in two separate steps. As the first step, the alkylation reaction, preferably with methyl bromide, may be carried out in order to block the hydroxyl group at carbon 5 of the flavone moiety of compound II. Then, as a second, separate step, the flavone moiety may be transformed into a chalcone moiety, so as to carry out the process of opening of the flavone moiety ring, with all hydroxyl substitutes of the flavone moiety blocked.

Notwithstanding the above, the method according to the invention enables one to carry out the two reactions: alkylation and formation of a chalcone moiety at the same time, in a common reaction 12 medium, which reduces the reaction time, the labour expenditure of the process, as well as the number of devices necessary for the implementation thereof. In reaction 12, as a result of using the reaction medium as described in detail below, the ring in the flavone moiety is opened at the step when all the hydroxy groups are blocked.

The blocking of all hydroxy groups substantially prevents cyclization reactions and potentially co-occurring isomerisation reactions. Thus, no undesirable by-products are formed in the XN synthesis process, and the xanthohumol obtained does not require purification on the chromatographic column.

The opening of the flavone moiety of compound II according to the method presented herein is carried out in an anhydrous solvent which is a polar aprotic solvent, or a mixture of several solvents of this type. The reaction is carried out in an alkaline environment, using a base that is non-nucleophilic under the determined conditions. The selection of the reaction conditions: a suitable solvent and a base, both provide a high selectivity of the reaction and a very good yield of compound III.

In the course of work aimed at improving the yield of reaction 12, it was observed that the best yield of the chalcone compound (compound III) is achieved when using methyl iodide (Mel) as the alkylating agent, DBU as the non-nucleophilic base and DMF as the solvent.

The chalcone compound (compound III) is then subjected to a hydrolysis reaction 13 involving the hydrolysis of ester moieties: —O—C(O)—$CH_3$ (—OAc), to obtain a chalcone compound product with hydroxy groups at carbons 4, 4' and 6' of the chalcone moiety (compound V).

Various alcohols may be used as the agent for hydrolysing ester moieties to hydroxyl groups, preferably C1-C8 alcohols, for example alcohols such as ethyl alcohol, methyl alcohol, propyl alcohol, isopropyl alcohol, butyl alcohol or isobutyl alcohol.

The hydrolysis reaction 13 is carried out in an alkaline environment, preferably at a pH range between 12 and 14, in the presence of a strong base, preferably a hydroxide of element of the lithium group or hydroxide of element of the calcium group, such as for example: KOH, NaOH, LiOH, carbonates of elements of the lithium group such as: $Na_2CO_3$, $K_2CO_3$ or alcoholates of elements of the lithium group or of elements of the calcium group such as for example: MeONa (sodium salt of methyl alcohol), t-BuOK (potassium salt of tert-butyl alcohol).

Very good yield of the hydrolysis reaction is obtained when using ethyl alcohol as a hydrolysing agent in the presence of KOH. Reaction in such conditions carried out in room temperature for 2 hours has a 100% yield.

Compound V is then subjected to reaction 14 to form xanthohumol: compound VI. In prenylation reaction 14, a prenyl group ($—CH_2—CH═C—(CH_3)_2$) is substituted to carbon 3 of the chalcone moiety.

Various compounds may be used as the donor of prenyl group used, i.e. the donor which allows for substitution of the prenyl group in the chalcone structure, for example, the donor of prenyl group may comprise 1,1-dimethylallyl moiety; for example: 1,1-dimethylalyl alcohol or the ester of acetic acid and 1,1-dimethylallyl alcohol may be used as the donor of prenyl group.

The reaction is carried out in the presence of a catalyst, preferably boron trifluoride etherate ($BF_3{\cdot}O(CH_2CH_3)_2$, CAS no. of the compound: 109-63-7).

Reaction 14 is carried out in an organic solvent, preferably selected from the group consisting of: dioxane, tetrahydrofuran (THF), 1,2-dimethoxyethane and toluene.

Preferably, reaction 14 is carried out at an elevated temperature in the range between 30 and 150° C., and more preferably, at 40° C., preferably subsequently using column chromatography in order to purify the reaction product.

The slightly elevated temperature ensures a higher reaction yield. In the course of the research carried out, it was unexpectedly discovered that a very good yield of reaction 14: prenylation of the chalcone moiety to form xanthohumol is obtained when using 1,1-dimethylallyl alcohol as the prenylating agent in the presence of boron trifluoride etherate, in a dioxane medium—as a solvent, maintaining the temperature of 40° C. Under these conditions, reaction 14 has a yield of approximately 35%. The reaction time is preferably 2 hours.

Reaction product 14: xanthohumol, marked in FIG. 1 as compound VI, can be purified by way of crystallization thereof, which is a well-known and inexpensive isolation method. This is due to the absence of poorly removable contaminations in the post-reaction mixture, such as, for example, isoxanthohumol, which is impossible to separate by way of crystallisation.

The total yield achievable with the method according to the invention is approximately 13%. A significant advantage of the developed synthesis route is also the elimination of the need to purify the product: XN on the chromatographic column.

Accordingly, the synthesis is particularly suitable for the production of XN on an industrial scale, but it can also be used on a smaller scale, including laboratory or semi-technical, as needed.

XN obtained by the method of the invention has satisfactory purity and it may be used as an ingredient of various compositions, including cosmetic compositions, as their active ingredient.

Example Embodiment a) Synthesis of compound II: 4-(7-acetoxy-5-hydroxy-4-oxochroman-2-yl)phenyl acetate Acetic anhydride (1.88 mL, 20 mmol) was added dropwise to Naringenin (Compound I) solution (2.72 g, 10 mmol) in dry pyridine (10 mL) at room temperature. After adding it dropwise, the mixture was stirred for 2 hours. Then, the contents of the flask were poured onto a mixture of ice and water. Precipitate was formed, which was drained and then crystallised from methanol to obtain 2.02 g of the product with 57% yield.

The resulting product was analysed by 1H NMR to obtain the following 1H NMR spectrum (700 MHZ, $CDCl_3$) δ (ppm); 2.29 (s, 3H), 2.32 (s, 3H), 2.89 (dd, 1H, J=17.2 Hz, J=2.8 Hz), 3.10 (dd, 1H, J=17.2 Hz, J=13.2 Hz), 5.45 (dd, 1H, J=13.2 Hz, J=2.8 Hz), 6.30 (d, 1H, J=2.1 Hz), 6.31 (d, 1H, J=2.1 Hz), 7.16 (d, 2H, J=8.5 Hz), 7.46 (d, 2H, J=8.5 Hz), 11.83 (s, 1H).

b) Synthesis of compound III: (E)-4-(3-(4-acetoxyphenyl)acryloyl)-5-methoxy-1,3-phenylene diacetate 4(7-acetoxy-5-hydroxy-4-oxochroman-2-yl)phenyl acetate (Compound II) (4.0 g, 11.2 mmol) was placed in a thoroughly dried round-bottom flask, dissolved in dry N,N-dimethylformamide (DMF) (20 mL) under argon. DBU (2.5 mL, 16.8 mmol) was then added. This was heated to 50° C., after which methyl iodide (1.05 mL, 16.8 mmol) was added dropwise, followed by acetic anhydride (0.99 mL, 11.2 mmol). This was mixed at the indicated temperature for 2 h, until the substrate was no longer observed. The reaction was controlled using HPLC-MS. The reaction was terminated by adding water (50 mL) and extracted with ethyl acetate (3×30 mL). The combined extracts were washed with water (20 mL) and dried over anhydrous $MgSO_4$, filtered and evaporated. The raw product was purified on a Flash chromatographic column (petroleum ether/ethyl acetate eluent 7/3). 1.83 g of vivid yellow product was obtained with a yield of 44%.

The resulting product was analysed by 1H NMR to obtain the following 1H NMR spectrum (700 MHZ, $CDCl_3$) δ (ppm); 2.15 (s, 3H), 2.30 (s, 3H), 2.31 (s, 3H), 3.79 (s, 3H), 6.64 (d, 1H, J=1.4 Hz), 6.65 (d, 1H, J=1.4 Hz), 6.90 (d, 1H, J=16.1 Hz), 7.12 (d, 2H, J=8.4 Hz), 7.38 (d, 1H, J=16.1 Hz), 7.55 (d, 2H, J=8.4 Hz).

c) Synthesis of compound V: (E)-1-(2,4-Dihydroxy-6-methoxyphenyl)-3-(4-hydroxyphenyl)prop-2-en-1-on (E)-4-(3-(4-acetoxyphenyl)acryloyl)-5-methoxy-1,3-phenylene diacetate (Compound III) (1.60 g, 3.88 mmol) dissolved in EtOH (10 mL), and potassium hydroxide (0.44 g, 7.77 mmol) were placed in a round-bottom flask. This was stirred at room temperature for 2 hours. The reaction was controlled using HPLC-MS. When the substrate was no longer observed, 2M HCl (5 mL) was added to the mixture. The mixture was transferred to a separator and extracted with ethyl acetate (3×30 mL). The combined extracts were washed with water (20 mL) and dried over anhydrous $MgSO_4$, filtered and evaporated. A pure product was obtained, which is a yellow solid. Reaction yield 100% (1.05 g).

The resulting product was analysed by 1H NMR to obtain the following 1H NMR spectrum (700 MHz, $CDCl_3$) δ (ppm); 3.80 (s, 3H), 6.60 (d, 1H, J=1.5 Hz), 6.67 (d, 1H, J=1.5 Hz), 6.99 (d, 1H, J=16.0 Hz), 7.14 (d, 2H, J=8.5 Hz), 7.42 (d, 1H, J=16.0 Hz), 7.67 (d, 2H, J=8.5 Hz).

d) Synthesis of Compound VI: Xanthohumol (E)-1-(2,4-dihydroxy-6-methoxyphenyl)-3-(4-hydroxyphenyl)prop-2-en-1-on (Compound V) (2.86 g, 10 mmol), tetrahydrofuran (10 mL) and 1,1-dimethylallyl alcohol (1.03 g, 12 mmol) were placed in a thoroughly dried round-bottom flask under nitrogen. The mixture was heated to 40° C. and boron trifluoride etherate (2.50 ml, 20 mmol) was added dropwise. After adding it dropwise, the mixture was stirred for 2 hours, poured into water (30 mL) and extracted with ethyl acetate (3×15 mL). The combined extracts were washed with water (15 mL) and dried over anhydrous $MgSO_4$, filtered and evaporated. The raw product was purified on a Flash chromatographic column in hexane/AcOEt (1/1). 1.24 g of the product was obtained with a yield of 35%.

The resulting product was analysed by 1H NMR to obtain the following 1H NMR spectrum (700 MHz, $CD_3OD$), δ (ppm): 1.65 (bs, 3H), 1.76 (bs, 3H), 3.22 (d, J=7.3 Hz), 3.90 (s, 3H), 5.21-5.18 (m, 1H), 5.21-5.18 (m, 1H), 6.02 (s, 1H), 6.02 (s, 1H), 6.82 (d, J=8.6 Hz, 2H), 7.50 (d, J=8.6 Hz, 2H), 7.67 (d, J=15.5 Hz, 1H), 7.79 (d, J=15.5 Hz, 1H).

While the invention has been described with respect to a limited number of embodiments, it will be appreciated that many variations, modifications and other applications of the invention may be made. Therefore, the claimed invention as recited in the claims that follow is not limited to the embodiments described herein.

The invention claimed is:

1. A method for synthesizing xanthohumol (XN), the method comprising the steps of:
- providing naringenin,
- acylating hydroxyl groups at carbons 7 and 4' of a naringenin flavone moiety to obtain an acylation product,
- subjecting the acylation product to a reaction of alkylation of a free hydroxyl to an alkoxyl moiety and to a reaction of conversion of the naringenin flavone moiety into a chalcone moiety, in a presence of a non-nucleophilic base, in a polar aprotic solvent, to obtain a chalcone compound,
- subjecting the chalcone compound to:
  - a reaction of hydrolysis of its ester groups at carbons 4, 4' and 6 of the chalcone moiety to obtain hydroxyl groups, and next
  - a reaction of substitution of a prenyl moiety at carbon 5' of the chalcone moiety to obtain xanthohumol.

2. The method according to claim 1, comprising carrying out the step of acylating using acetic anhydride.

3. The method according to claim 1, comprising purifying the acylation product by way of crystallisation.

4. The method according to claim 1, comprising carrying out the reaction of alkylation using an alkylating agent selected from a group consisting of C1-C8 alkyl iodides and bromides.

5. The method according to claim 4, comprising carrying out the reaction of alkylation using the alkylating agent selected from a group consisting of methyl iodide and methyl bromide.

6. The method according to claim 1 comprising carrying out the reaction of conversion of the flavone moiety into the chalcone moiety in a presence of a non-nucleophilic base selected from a group consisting of: 1,8-diazabicyclo[5.4.0]undec-7-ene (DBU), 1,4-diazabicyclo[2.2.2]octane (DABCO) and 4-(N,N-dimethylamino) pyridine (DMAP).

7. The method according to claim 1, comprising carrying out the reaction of conversion of the flavone moiety into the chalcone moiety in a polar aprotic solvent selected from a group consisting of: dimethylformamide (DMF), N-methylpyrrolidone (NMP) and dimethylacetamide (DMAc).

8. The method according to claim 1, comprising subjecting the obtained chalcone compound to a hydrolysis reaction carried out using ethyl alcohol in an alkaline medium.

9. The method according to claim 1, comprising carrying out the substitution reaction of the prenyl moiety using a prenylating agent comprising 1,1-dimethylallyl moiety.

10. The method according to claim 9 wherein the prenylating agent used is 1,1-dimethylallyl alcohol or acetic acid ester of 1,1-dimethylallylalcohol.

11. The method according to claim 1, comprising carrying out the substitution reaction of the prenyl moiety in the presence of boron trifluoride etherate ($BF_3{\cdot}O(CH_2CH_3)_2$) in dioxane, at elevated temperature.

12. The method according to claim 11, comprising carrying out the substitution reaction at a temperature of 40° C.

* * * * *